United States Patent [19]

Carlsson et al.

[11] Patent Number: 4,563,304
[45] Date of Patent: Jan. 7, 1986

[54] PYRIDINE COMPOUNDS MODIFYING PROTEINS, POLYPEPTIDES OR POLYSACCHARIDES

[75] Inventors: Jan P. E. Carlsson, Upsala; Rolf E. A. V. Axén, Bälinge; Hakan N. Y. Drevin, Brunna; Göran E. S. Lindgren, Almunge, all of Sweden

[73] Assignee: Pharmacia Fine Chemicals AB, Upsala, Sweden

[21] Appl. No.: 582,911

[22] Filed: Feb. 23, 1984

Related U.S. Application Data

[60] Continuation of Ser. No. 238,853, Feb. 27, 1981, abandoned, which is a continuation of Ser. No. 98,302, Nov. 28, 1979, abandoned, which is a continuation of Ser. No. 946,140, Sep. 27, 1978, abandoned, which is a division of Ser. No. 882,546, Mar. 2, 1978, Pat. No. 4,149,033.

[51] Int. Cl.[4] .................. C07G 7/00; C07H 1/00; C12N 9/26; C07B 37/00
[52] U.S. Cl. .................. 260/112 R; 260/112 B; 260/121; 435/177; 435/188; 536/1.1; 536/53; 424/85
[58] Field of Search .............. 260/112 R, 112 B, 121; 536/1, 53; 435/177, 188; 424/85

[56] References Cited

U.S. PATENT DOCUMENTS 4,149,003  4/1979  Carlsson et al. ............ 260/112 R X

OTHER PUBLICATIONS

Chem. Abstracts vol. 90, 1979, 18765w, Carlsson et al., effective date 9/78.
Chem. Abstracts vol. 90, 1979, 181773f, Carlsson et al., effective date 1978.
Biochemical J., Sep., 1978, 173(3), 723–737, Carlsson et al.

Primary Examiner—Howard E. Schain
Attorney, Agent, or Firm—Fred Philpitt

[57] ABSTRACT

Novel pyridine compounds having the formula $R^1$-S-S-A-Z are disclosed, in which formula $R^1$ is 2-pyridyl, 5-nitro-2-pyridyl or 4-pyridyl, A is a hydrocarbon residue having 1–10 carbon atoms and Z is a group

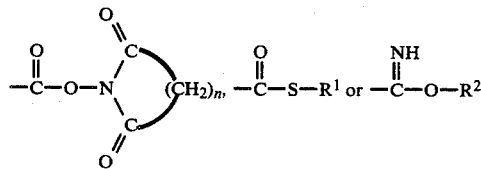

or acid addition salts of the last mentioned group, where n is 2 or 3, $R^1$ has the same significance as $R^1$ above and is equal thereto and $R^2$ is methyl or ethyl. These compounds are particularly useful as bifunctional coupling agents and as thiolating agents.

5 Claims, No Drawings

PYRIDINE COMPOUNDS MODIFYING PROTEINS, POLYPEPTIDES OR POLYSACCHARIDES

RELATED APPLICATIONS

This application is a continuation of Ser. No. 238,853 (filed Feb. 27, 1981), now abandoned, which in turn was a continuation of Ser. No. 98,302 (filed Nov. 28, 1979), now abandoned, which in turn was a continuation of Ser. No. 946,140 (filed Sept. 27, 1978), now abandoned, which in turn was a division of Ser. No. 882,546 (filed Mar. 2, 1978), now U.S. Pat. No. 4,149,033. The benefits of 35 USC 120 are claimed relative to these applications.

The present invention relates to novel pyridine compounds.

The novel compounds according to the invention are in particular useful as bifunctional coupling agents and as thiolating agents.

It is known in the preparation of conjugates of two substances, of which at least one comprises a protein or a polypeptide, to use bifunctional agents in order to couple the components of the conjugate covalently, amino groups in the conjugated molecules normally being utilized for the conjugating reaction. A popular agent in this connection is glutardialdehyde. A protein or a polypeptide, however, normally contains more than one amino group, whilst the substance comprising the second component of the conjugate may also contain more than one amino group. When coupling with glutardialdehyde and other bifunctional agents utilizing amino groups in the conjugated molecules, in addition to obtaining the desired reaction to form a conjugate of determined composition (e.g. a bimolecular conjugate containing only a single molecule of each component) there are also obtained subsidiary reactions which lead to intramolecular cross-linking in the protein or the polypeptide, or to the formation of conjugates having two molecules of the same component type or three or more molecules of one or both types of molecule, and, in certain cases, also to the polymerisation of the coupling agent (e.g. when glutardialdehyde is used) to form aggregates which may be of approximately the same size as the conjugates. Thus, there is obtained a most heterogeneous product mixture. It is only possible to obtain a conjugate of satisfactory unitariness and purity by using special reaction conditions and purifying the reaction mixture with such types of separation methods as affinity chromatography and gel filtration, but these methods involve much work and are relatively time consuming. Furthermore, the yields are often very low.

In accordance with the invention there has now been discovered a new group of compounds which can be used as bifunctional agents for the manufacture, under mild conditions, of relatively unitary both homo- and hetero-conjugates of bimolecular or oligomeric nature without, as in the case of the known agents, giving rise to subsidiary reactions. Consequently, when using the novel coupling agents there is obtained a higher hield of the desired conjugate.

The new compounds can also be used as thiolating agents for thiolating substances which contain amino groups. This is particularly favourable in relation to macromolecular substances containing amino groups and being soluble in aqueous liquids, particularly biopolymers and derivatives thereof containing amino groups, primarily proteins, polypeptides and polysaccharides or derivatives thereof, which contain amino groups.

The compounds according to the present invention are characterized by the fact that they have the formula

in which $R^1$ is 2-pyridyl, 5-nitro-2-pyridyl or 4-pyridyl, A is a hydrocarbon residue having 1-10 carbon atoms, preferably 1-6 carbon atoms, and Z is a group

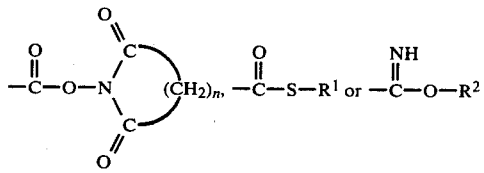

or acid addition salts of the lastmentioned group, where n is 2 or 3, $R^1$ has the same significance as $R^1$ above and is equal thereto and $R^2$ is methyl or ethyl.

The hydrocarbon residue A is preferably an aliphatic residue but may also be an aromatic residue. A is for example a straight or branched alkylene residue, e.g. $-(CH_2)_m-$, wherein m is an integer 1-10, preferably 1-6, for example $-CH_2-CH_2-$.

The compounds of formula I can be prepared in a number of different ways. The methods preferred today are the following:

Compounds of the formula I, in which Z is the group

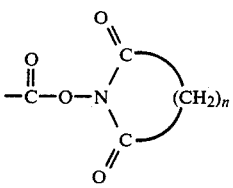

are prepared by reacting a disulphide of the formula

where $R^1$ and A both have the above given significance, with N-hydroxysuccinimide when n=2 (or the analogous compound with n=3 when compounds with n=3 are desired) in the presence of a condensating agent.

The reaction is carried out in an organic solvent at a temperature of 10°-30° C. A suitable solvent is, for example, methylene chloride, ethylene acetate and dioxane. The reaction time varies with the choice of reaction components and reaction temperature.

The condensating agent used may be one which is common in esterifying reactions, for example N,N'-dicyclohexylcarbodiimide.

The starting compound of the formula II can be prepared by reacting a mercaptoalkyl carboxylic acid of the formula

with a dipyridyl disulphide of the formula

in which formulae A and $R^1$ both have the aforestated significance.

This reaction is carried out in an organic solvent at a temperature of 10°–30° C. A suitable solvent is, for example, ethanol, ethyl acetate and dioxane. The reaction time varies with the selection of reaction components and the reaction temperature.

Compounds of the formula I, in which Z is the group

are prepared by reacting a disulphide of formula II above with a corresponding thiopyridone in the presence of a condensing agent in an organic solvent at an initially low temperature, for example −20° C., for approximately 1–2 hrs, and thereafter at ambient temperature (about +20° C.). A suitable solvent in this respect, is for example, methylene chloride, ethyl acetate and dioxane. The condensing agent used is preferably N,N'-dicyclohexylcarbodiimide.

The starting material used is preferably a mixture obtained by reacting a compound of formula III with a compound of Formula IV.

Compounds of the formula I, in which Z is the group

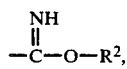

are prepared by reacting a thiolimidate of the formula

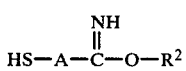

in which $R^2$ and A have the aforementioned significance, with a pyridyl disulphide of the formula $R^1$—S—S—$R^1$, in which $R^1$ has the above significance, in an organic solvent. The solvent, for example, may be methanol containing approximately 10% glacial acetic acid.

When using the compounds according to the invention as bifunctional coupling agents, the following method is applied. By way of example there have been selected two substances for coupling, each of which has accessible to the reaction at least one amino group (e.g. proteins and peptides) and which can generally be designated $B_1$—$NH_2$ and $B_2$—$NH_2$, with the aid of N-succinimidyl-3-(2-pyridyldithio)-propionate

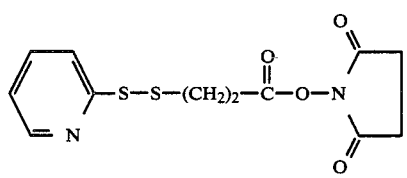

in accordance with the invention.

The two substances are first each reacted with the agent according to

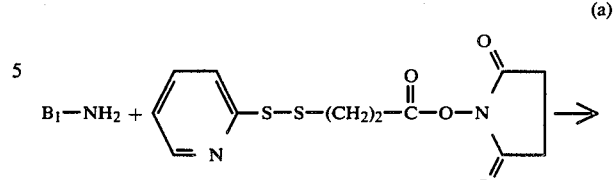

(a)

and (b)

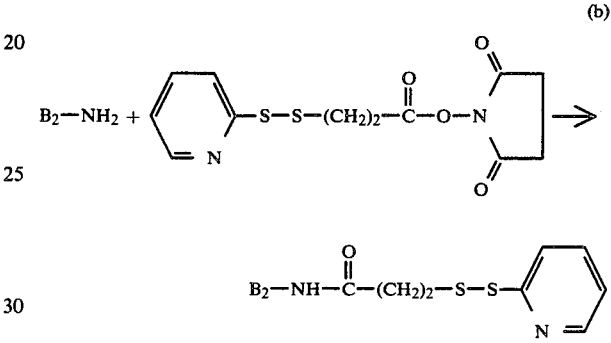

respectively.

One of these products, e.g. the product from step (b) is then reduced with, for example, dithithreitol (DTT) in an acid medium in accordance with

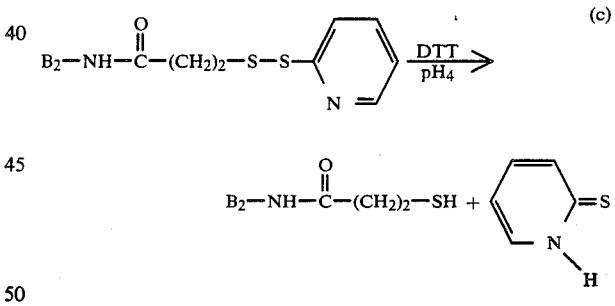

(c)

The thus obtained thiol is then reacted with the disulphide from, in this case, the step (a) in accordance with

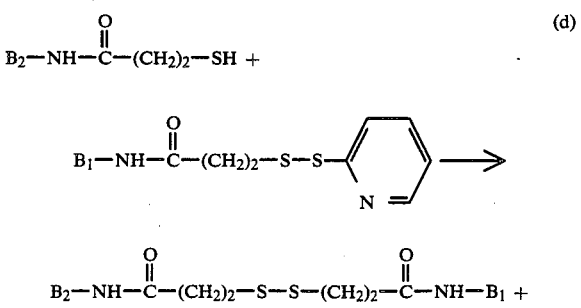

(d)

-continued

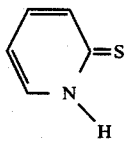

Steps (a) and (b) are carried out in an aqueous solution at a pH of from 5-8 and containing 1-10 percent by volume MeOH or EtOH at a temperature of normally 20°-25° C.

Step (c) can be carried out in an aqueous medium at pH 3-5 and a temperature of normally 20°-25° C. If the modified molecule $B_2$ does not contain native disulphide bonds, the reduction may also be carried out with other reducing agents and at higher pH-values, for example up to pH 8 to 8.5.

Step (d) is normally carried out in an aqueous medium at pH 4-8 and a temperature of 20°-25° C.

If one of the substances already contains a reactive thiol group (e.g. an aliphatic thiol group) accessible for the reaction, the steps (b) and (c) above can be omitted.

If a bimolecular heteroconjugate is desired, the two substances should not be substituted more than to approximately monosubstitution. When desired, a greater conjugate than bimolecular can be prepared by substituting the two substances with more than one substituent group per molecule. A requisite herewith is, naturally, that the substances contain a corresponding number of amino groups accessible for the reaction. In the synthesis of oligo-conjugates (e.g. tri- and tetra-conjugates) one of the substances should not generally be substituted more than to approximately monosubstitution. It is also possible to prepare homo-conjugates (i.e. $B_1 = B_2$) in the same manner as that described above.

The use of the compounds according to the invention as thiolating agents is evident from steps (b) and (c) above. It is particularly favourable in this respect that the introduced thiol group is blocked in pyridyldisulphide form. In this way undesirable thiol disulphide exchange reactions between the introduced thiol group and any disulphide bridges present in the substance (e.g. when the substance is a protein or a polypeptide containing disulphide bridges) are avoided during the modification step and when storing the modified substance, e.g. modified protein. When it is desired to convert the $R^1$—S—S—group introduced into the substance (e.g. protein) to a thiol group (HS—), this can be effected by selective reduction without, at the same time, reducing any native disulphide bridges which may be present in the substance. This is possible owing to the difference in chemical reactivity between the $R^1$—S—S—group and, e.g., native aliphatic disulphide bridges in proteins.

Thus, the invention also includes modified macromolecular substances soluble in aqueous liquids, particularly biopolymers and derivatives thereof containing amino groups, preferably proteins, polypeptides and polysaccharides or derivatives thereof, which contain amino groups. These modified macromolecular substances are characterized in that one or more amino groups (—NH₂) therein have been converted to a group of the formula

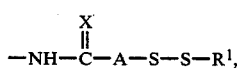

in which A and $R^1$ both have the above significance and X is O or NH, preferably O. Preferably said groups are selected from groups of the formula

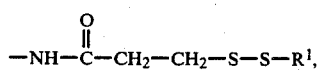

in which $R^1$ has the above significance, preferably 2-pyridyl.

The thiol-disulphide exchange reactions according to steps (c) and (d) require that the group $R^1$ in the compound of formula I can be split-off reductively to the compound $R^1$—SH, which is tautomerised to the corresponding compound $HR^1$=S. In addition to being fulfilled by the groups 2-pyridyl and 4-pyridyl, the condition is also fulfilled by corresponding groups substituted with a substituent of such type and in such position that the thiol-thion-tautomerism is not destroyed. 5-nitro-2-pyridyl has been found to belong to this substituted pyridyl groups.

The invention will now be illustrated further with reference to a number of examples, which illustrate the preparation of compounds in accordance with the invention, and examples of the use of these compounds.

EXAMPLE 1

N-succinimidyl-3(2-pyridyldithio)propionate 1.9 g (8.6 mmole) 2,2'-dipyridyldisulphide were dissolved in 10 ml of ethyl acetate. A solution of 0.9 g (8.6 mmole) 3-mercaptopropionic acid in 10 ml of ethyl acetate was added dropwise for 15 minutes whilst stirring, at the same time as 0.1 ml (2 drops) of boron trifluoride etherate was added to the reaction mixture. Subsequent to remaining for 20 hours at room temperature whilst being agitated, the reaction mixture was vaporized (Büchi Rotavapor, <40° C.) and the solid yellow residue was slurried with 10 ml (cold) (+4° C.) ethyl acetate and filtered. In this way there was recovered approximately 90% 2-thiopyridone (mp 124°-126° C., Lit. 128°-130° C.). The yield of 2-carboxyethyl(2-pyridyl)disulphide was approximately 60%. ¹H—NMR δ (CDCl₃) 2.7-3.3 (4H, m, —CH₂CH₂—), 6.90-8.5 (4H, m,

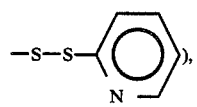

12.5 (1H, s, —COOH).

0.68 g (5 mmole) of N-hydroxysuccinimide were then added to the solution, whereafter 1.03 g (5 mmole) of dicyclohexylcarbodiimide dissolved in 10 ml dry ethyl acetate were added dropwise for 15 minutes whilst agitating at room temperature. The reaction was permitted to continue under agitation for 5 hrs at room temperature, whereafter the reaction mixture was cooled to +4° C. and the precipitated dicyclohexylcarbamide was filtered off. The slightly yellow solution was vaporized and the oil dissolved in ethanol and permitted to crystallize at −20° C. The yield was 45%. The melting point was 78.5°-80.5° C.

¹H—NMR δ (CDCl₃) 2.83 (4H, s,

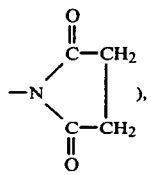

3.12 (4H, s broad, —CH₂—CH₂—), 6.90–8.82 (4H, m,

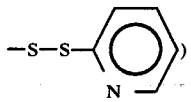

Calculated for C₁₂H₁₂N₂O₄S₂: C, 46.14; H, 3.83; N, 8.97; S, 20.53% Found: C, 46.19; H, 3.88; N, 8.96; S, 20.02%.

EXAMPLE 2

2-thiopyridyl-3-(2-pyridyldithio)propionate 1.9 g (8.6 mmole) of 2.2′-dipyridyl disulphide were dissolved in 65 ml of ethyl acetate. A solution of 0.9 g (8.6 mmole) 3-mercaptopropionic acid in 10 ml ethyl acetate were added dropwise for 15 minutes under agitation, at the same time as 0.1 ml (2 drops) of boron trifluoride etherate was added to the reaction mixture. After 20 hours at room temperature, the solution was cooled to −20° C. Thereafter 1.03 g (5 mmole) of dicyclohexylcarbodiimide was dissolved in 15 ml of ethyl acetate and added dropwise to the solution for 15 minutes whilst being strongly stirred. The reaction was allowed to continue at −20° C. for one hour and then at room temperature (about 20° C.) over night. The resultant dicyclohexylcarbamide was filtered off and the solution vaporized (Büchi Rotavapor, <40° C.). Thereafter 10 ml cold (+4° C.) ethyl acetate were added and the mixture again filtered, whereupon all the dicyclohexylcarbamide could be removed. The product weighed 1.5 g. Purity approximately 90%.

¹H—NMR, δ (CDCl₃) 3.15 (4H, s broad, —CH₂—CH₂—), 6.90–8.8 (8H, m,

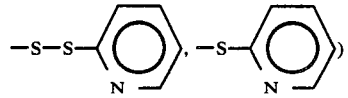

EXAMPLE 3

Methyl-4(2-pyridyldithio)butyrimidate 20 mg (0.12 mmole) of methyl-4-mercaptobutyrimidatehydrochloride, 26 mg (0.12 mmole) 2,2′-dipyridyl disulphide and 0.5 ml of glacial acetic acid were dissolved in 5 ml of methanol. The reaction was followed with ¹H—NMR and when all the imidate has reacted (approximately 12 hours) the mixture was vaporized to dryness. Analysis of the reaction mixture with the aid of ¹H—NMR (CD₃OD) showed a yield of approx. 20% based on methyl-4-mercaptobutyrimidate.

EXAMPLE 4

N-succinimidyl-2(2-pyridyldithio)-propionate

This compound was prepared in the same way as the N-succinimidyl-3(2-pyridyldithio)propionate described in Example 1 but the 3-mercaptopropionic acid was replaced by 2-mercaptopropionic acid. Furthermore, the synthesis was carried in about 1/10 scale. The product was analysed with ¹H—NMR:

| R¹ | δ(ppm) | A | δ(ppm) | Z | δ(ppm) |
|---|---|---|---|---|---|
| ![pyridyl-S-] | 6.8–8.7 m | CH₃<br>\|<br>—CH— | 1.55 d<br>4.12 q | ![succinimidyl -C(=O)-O-N(C=O)₂] | 2.72 s |

EXAMPLE 5

N-succinimidyl-3(4-pyridyldithio)propionate

This compound was prepared in the same way as the N-succinimidyl-3(2-pyridyldithio)-propionate described in Example 1 but the 2,2′-dipyridyl disulphide was replaced by 4,4′-dipyridyl disulphide. Furthermore, the synthesis was carried out in 1/10 scale. The product was analysed with ¹H—NMR:

| R¹ | δ(ppm) | A | δ(ppm) | A | δ(ppm) |
|---|---|---|---|---|---|
| ![4-pyridyl-S-] | 7.3–8.7 m | CH₃<br>\|<br>—CH— | 1.6 d<br>4.10 q | ![succinimidyl -C(=O)-O-N(C=O)₂] | 2.69 s |

EXAMPLE 6

N-succinimidyl-3(5-nitro-2-pyridyldithio)propionate

This compound was prepared in the same way as the N-succinimidyl-3(2-pyridyldithio)propionate described in Example 1 but the 2,2′-dipyridyl disulphide was replaced by bis-(5-nitro-2-pyridyl)disulphide. Furthermore, the synthesis was carried out in 1/10 scale. The product was analysed with ¹H—NMR:

| R¹ | δ(ppm) | A | δ(ppm) | Z | δ(ppm) |
|---|---|---|---|---|---|
| O₂N—C₆H₃(N)—S— | 7.6–9.3 m | CH₃ \| —CH— | 1.6 d 4.10 q | —C(=O)—N(C=O)(C=O) (succinimidyl) | 2.70 s |

EXAMPLE 7

Thiolation of α-amylase 5 mg of α-amylase were dissolved in 0.5 ml of 0.1M Na-phosphate buffer, pH 7.5, 75 μl N-succinimidyl-3(2-pyridyldithio)propionate (34 mM in 99.5% EtOH) were added. Subsequent to vigorously shaking the mixture, the reaction was permitted to continue for 40 minutes at +23° C. The reaction mixture was gel filtered on Sephadex ® G-25 (beads of dextran cross-linked with epichlorohydrin from Pharmacia Fine Chemicals AB, Uppsala, Sweden) (the medium used was 0.3M Na-phosphate buffer, pH 7.5). The thus obtained α-amylase-pyridyl disulphide derivative was then reduced by adding 50 μl of 50 mM dithiothreitol to the material obtained from the gel filtration (1.5 ml). The reduction was permitted to continue for 20 minutes at +23° C. Surplus dithiothreitol and other low-molecular weight components were removed by gel filtration on Sephadex ® G-25 (the medium used was 0.3M NaCl). The thus thiolated α-amylase was found to contain 0.75 mole SH/mole protein.

EXAMPLE 8

Preparation of sheep-antirabbit IgG antibody-α-amylase conjugate (a) Thiolated α-amylase was prepared in accordance with Example 7 above.

(b) Sheep-antirabbit-IgG-antibodies containing 2-pyridyl disulphide groups 1.2 mg sheep-antibodies-IgG-antibodies (prepared from sheep-hyperimmune serum by immunosorbent purification) were dissolved in 0.5 ml of 0.1M Na-phosphate buffer, pH 7.5. 15 μl N-succinimidyl-3(2-pyridyldithio)-propionate (5.9 mM in EtOH) was added. Subsequent to shaking the solution vigorously, the reaction was allowed to take place for 40 minutes at +23° C. Surplus reagent and other undesired low molecular components were removed by gel filtration on Sephadex ® G-25 (beads of dextran cross-linked with epichlorohydrin from Pharmacia Fine Chemicals AB, Uppsala, Sweden) (medium 0.3M NaCl).

The thus modified sheep-antirabbit-IgG-antibodies were found to contain 2 mole 2-pyridyl disulphide groups/mole protein.

(c) Sheep-antirabbit-IgG-antibody-α-amylase conjugate 1.2 mg of sheep-antirabbit-IgG-antibody-2-pyridyl disulphide (8 mmole protein containin 17 nmole 2-pyridyl disulphide groups) (from (b) above) in 1 ml 0.3M NaCl were mixed with 5 mg of thiolated α-amylase (100 nmole containing 75 nmole SH-groups) (from (a) above) in 2 ml 0.3M NaCl. 0.1 ml of 0.1M Na-phosphate buffer, pH 7.5, were added and the reaction was permitted to take place for 18 hrs at +4° C.

Gel filtration on Sephadex ® G-200 of the reaction mixture and analysis of the fractions showed that 80% of the applied antibodies had conjugated. The conjugate thus formed was substantially bimolecular. Minor quantities of tri- and termolecular material could also be observed. The conjugate exhibited both enzymatic and immunologic activity. Fractions containing conjugates were combined and concentrated to 290 μg (conjugated antibodies)/ml and stored in 0.3M NaCl at +4° C.

EXAMPLE 9

Alkaline phosphatase containing 2-pyridyl disulphide groups 4 mg of alkaline phosphatase (from calf intestine, Boehringer Mannheim AG, West Germany) were dissolved in 2 ml of 0.1 m Na-phosphate buffer, pH 7.5. 150 μl of N-succinimidyl-3(2-pyridyldithio)propionate (1.7 mM in 99.5% ethanol) were added. Subsequent to vigorously shaking the reaction mixture, the reaction was permitted to continue for 40 minutes at +23° C. The reaction mixture was then gel filtered on Sephadex ® G-25 (the medium used was the same phosphate buffer as above).

The thus modified alkaline phosphatase contained 1 mole pyridyl disulphide structures/mole protein.

EXAMPLE 10

Thiolation of sheep-antirabbit-IgG-antibodies 2.5 mg sheep-antirabbitIgG-antibodies (prepared from sheep-serum by Na₂SO₄-precipitation) were dissolved in 0.5 ml of 0.1M Na-phosphate buffer, pH 7.5. 40 μl of N-succinimidyl-3(2-pyridyldithio)-propionate (1.7 mM in 99.5% ethanol) were added. After shaking the mixture vigorously, the reaction was permitted to continue for 40 minutes at +23° C. Surplus reactant and other undesirable low molecular weight components were removed by gel filtration on Sephadex ® G-25 (the medium used was 0.1M Na-acetate buffer pH 5). The thus obtained sheep antirabbitIgG-antibody-pyridyl disulphide derivative was then reduced by adding 50 μl of 50 mM dithiothreitol to the void material from the gel filtration (approx. 1.5 ml). The reduction was continued for 30 minutes at +23° C. Surplus dithiothreitol and other low molecular weight components were removed by gel filtration on Sephadex ® G-25 (the medium used was 0.3M NaCl). The thus thiolated sheep antirabbitIgG-antibodies contained 2 mole SH/mole protein.

EXAMPLE 11

Albumin containing 2-pyridyl disulphide groups 8 mg of human serum albumin in 1 ml of 0.1M Na-phosphate buffer, pH 7.5, were admixed with 12 μl N-succinimidyl-3(2-pyridyldithio)propionate (40 mM in 99.5% ethanol). After reaction for 40 minutes at +23° C. the reaction mixture was gel filtered on a column of Sephadex ® G-25 (the medium used was the same phosphate buffer as above). The void material, about 2 ml, contained the albumin-2-pyridyl disulphide derivative. A spectrophotometrical determination of the amount of liberated 2-thiopyridone after reduction of the derivative showed that the degree of substitution was 2.5 mole thiol/mole albumin.

What is claimed is:

1. A modified protein, polypeptide, polysaccharide or polysaccharide derivative containing amino groups and being soluble in aqueous liquids, wherein at least one amino group (—NH$_2$) of said protein, polypeptide, polysaccharide or polysaccharide derivative has been converted to a group of the formula

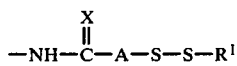

wherein $R^1$ is 2-pyridyl, 5-nitro-2-pyridyl or 4-pyridyl, A is a hydrocarbon residue having 1–10 carbon atoms and X is O or NH, by reaction with a compound having the formula

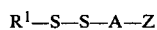

wherein $R^1$ and A are as defined above and Z is from the group

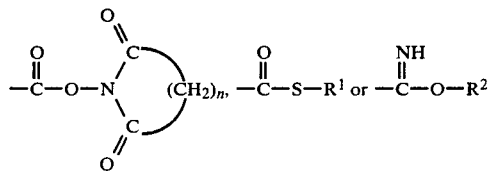

or acid addition salts of the last mentioned group, where n is 2 or 3, $R^1$ has the same significance as $R^1$ above and is equal thereto, and $R^2$ is methyl or ethyl.

2. A modified protein, polypeptide, polysaccharide or polysaccharide derivative containing amino groups according to claim 1, wherein A is a hydrocarbon residue containing 1–6 carbon atoms.

3. A modified protein, polypeptide, polysaccharide or polysaccharide derivative containing amino groups and being soluble in aqueous liquids, wherein at least one amino group (—NH$_2$) of said protein, polypeptide, polysaccharide or polysaccharide derivative has been converted to a group of the formula

wherein $R^1$ is 2-pyridyl,5-nitro-2-pyridyl or 4-pyridyl and A is a hydrocarbon residue of 1–6 carbon atoms, by reaction with a compound having the formula

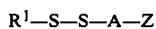

wherein $R^1$ and A are as defined above and Z is either

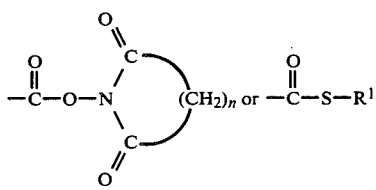

where n is 2 or 3 and $R^1$ has the same significance as $R^1$ above and is equal thereto.

4. A modified protein, polypeptide, polysaccharide or polysaccharide derivative containing amino groups according to claim 3 wherein A is —CH$_2$—CH$_2$—.

5. A modified protein, polypeptide, polysaccharide or polysaccharide derivative containing amino groups according to claim 4 wherein $R^1$ is 2-pyridyl.

* * * * *